United States Patent [19]

Johnson, Jr. et al.

[11] Patent Number: 5,113,877
[45] Date of Patent: May 19, 1992

[54] ANKLE SPRAIN MANAGEMENT SYSTEM

[75] Inventors: Glenn W. Johnson, Jr., Summit; Henry J. McVicker, Chatham, both of N.J.

[73] Assignee: Aircast Incorporated, Summit, N.J.

[21] Appl. No.: 665,604

[22] Filed: Mar. 6, 1991

[51] Int. Cl.⁵ .................................................. A61F 5/01
[52] U.S. Cl. ..................................... 128/882; 128/369; 128/399; 602/27
[58] Field of Search .................... 128/80 R, 80 H, 594, 128/846, 882, 166, 68.1, 362, 379, 382, 384, 399, 400, 401, 402, 403

[56] References Cited

U.S. PATENT DOCUMENTS

| | | |
|---|---|---|
| 2,595,328 | 5/1952 | Bowen . |
| 2,602,302 | 7/1952 | Poux ................................ 128/402 X |
| 2,749,914 | 6/1956 | Braley ................................ 128/402 |
| 3,548,819 | 12/1970 | Davis et al. . |
| 4,280,489 | 7/1981 | Johnson, Jr. . |
| 4,323,058 | 4/1982 | Detty ................................ 128/80 H |
| 4,427,010 | 1/1984 | Marx ................................ 128/399 X |
| 4,537,184 | 8/1985 | Williams, Jr. ..................... 128/402 X |
| 4,576,169 | 3/1986 | Williams ........................... 128/402 |
| 4,590,932 | 5/1986 | Wilkerson . |
| 4,729,370 | 3/1988 | Kallassy ........................... 128/80 H X |
| 4,846,176 | 7/1989 | Golden ............................. 128/384 X |
| 5,035,241 | 7/1991 | Walasek et al. ................... 128/403 |

OTHER PUBLICATIONS

"Ankle Compression Variability Using the Elastic Wrap, Elastic Wrap with a Horseshoe, Edema II Boot and Air Stirrup Brace", Duffley, et al, Athletic Training, Winter 1989, pp. 320-323.
"Treatment of Ankle Sprains with External Compression and Early Mobilization", Wilkerson, The Physician and Sports Medicine, vol. 13, No. 6, Jun. 1985, pp. 83-90.
"External Compression for Controlling Traumatic Edema", Wilkerson, The Physician and Sports Medicine, vol. 13, No. 6, Jun. 1985, pp. 97-106.
"Therapeutic Heat and Cold for Athletic Injuries", Halverson, The Physician and Sports Medicine, vol. 18, No. 5, May 1990, pp. 87-94.

*Primary Examiner*—Robert A. Hafer
*Assistant Examiner*—Sam Rimell
*Attorney, Agent, or Firm*—Jones, Day, Reavis & Pogue

[57] ABSTRACT

A generally U-shaped thermal compress having a compartment divided into first and second chambers by a common wall. One of the chambers holds a first liquid that freezes before a second liquid in the adjacent chamber. After the first liquid is frozen, the chamber having the second liquid is placed against the ankle. The U-shaped compress has a strap extending at an angle from one of the upper outer ends thereof to wrap around the ankle and attach to the other upper outer end to hold the compress in place. An elongated strap extending from the bottom of the U-shaped compress passes under the foot and around the ankle several times over the compress not only to hold the compress in place, but also to provide added compression to the forefoot for the control of edema. A soft insulating material is placed on the outside of the outer chamber having the ice therein to protect the ice from the effects of ambient temperature. The invention also includes a U-shaped stirrup so constructed that one of the side wall portions of the stirrup can fit over the compress that is placed around the ankle such that the foot with the stirrup and compress can be inserted in a shoe.

20 Claims, 5 Drawing Sheets

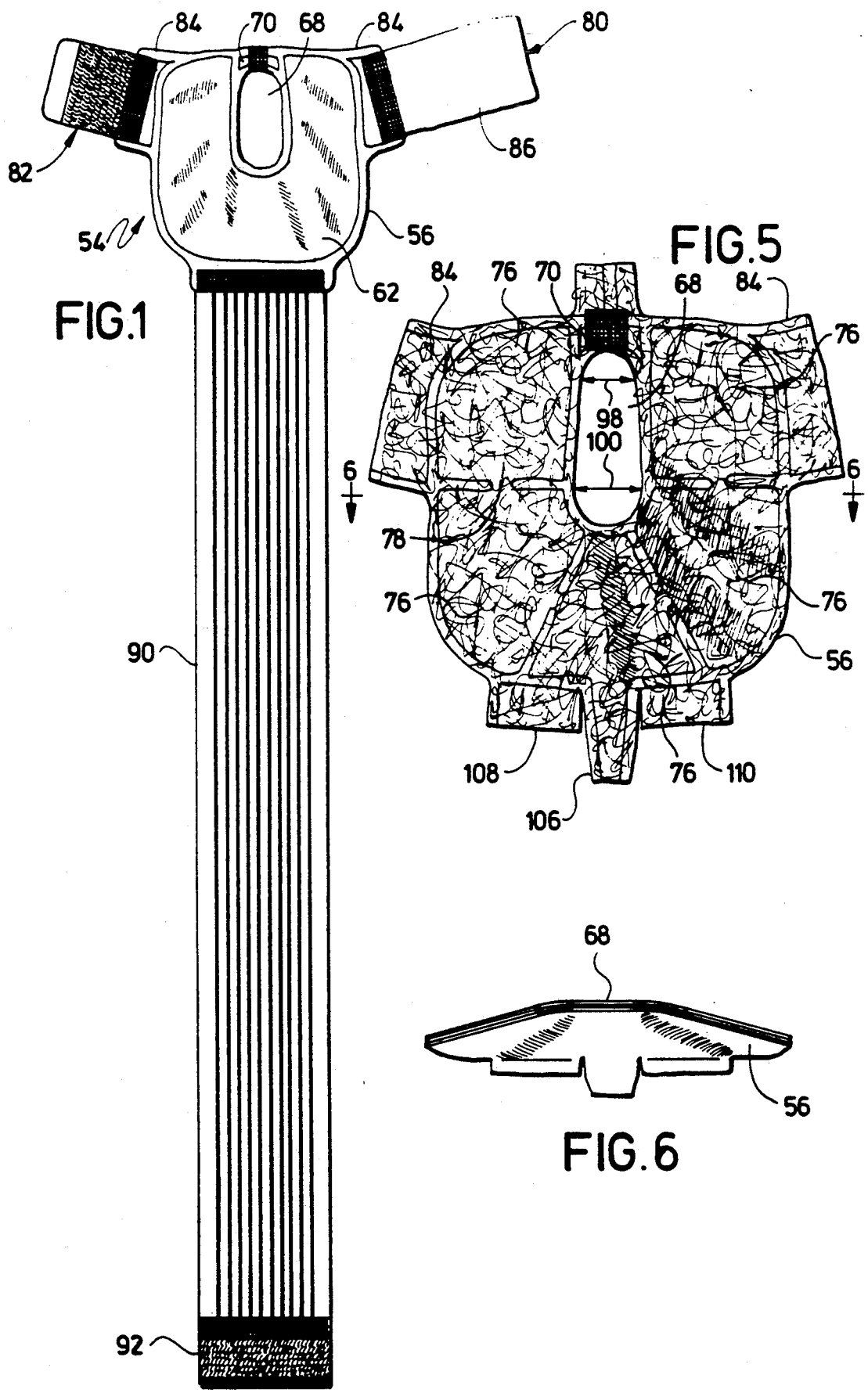

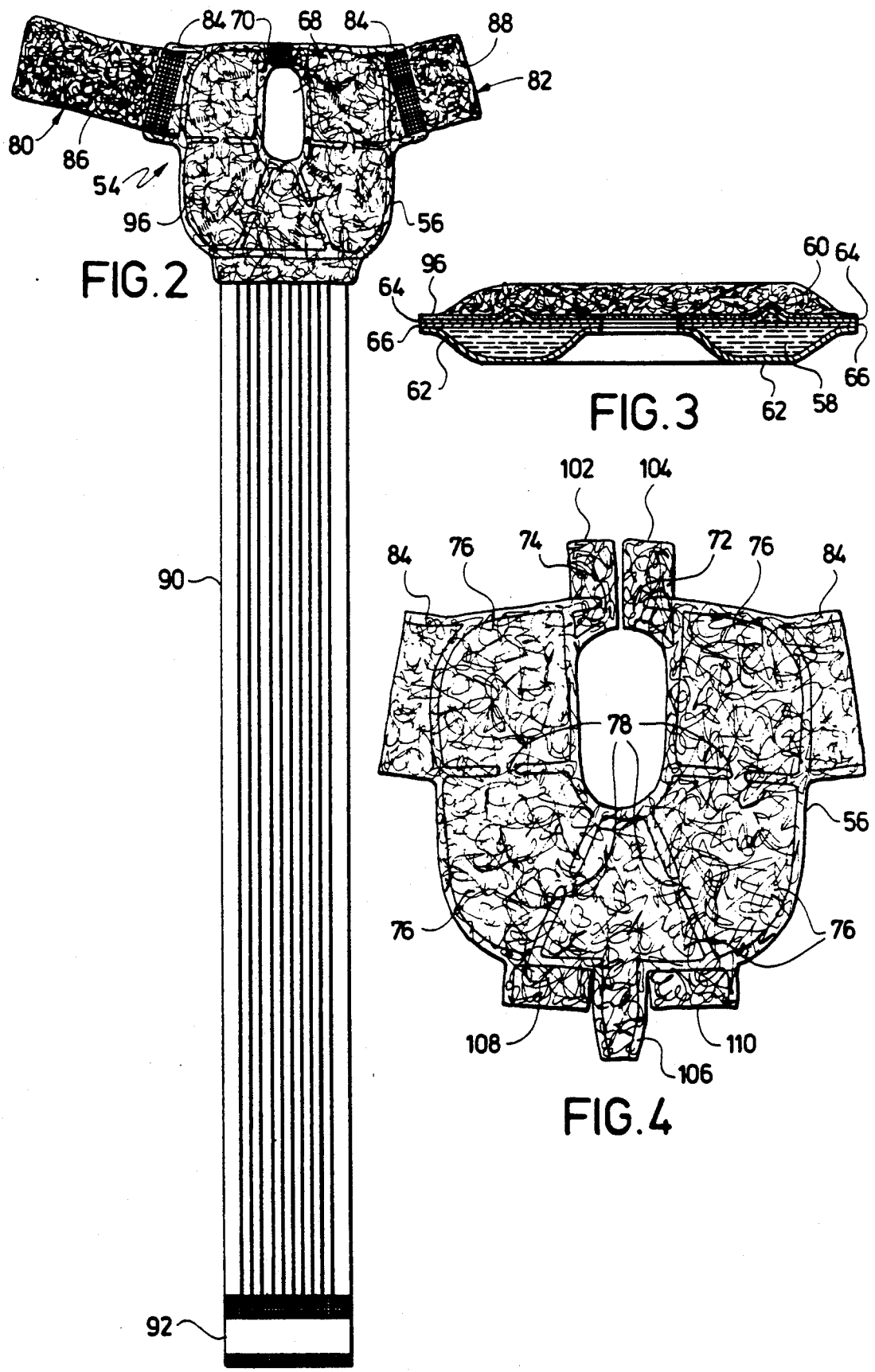

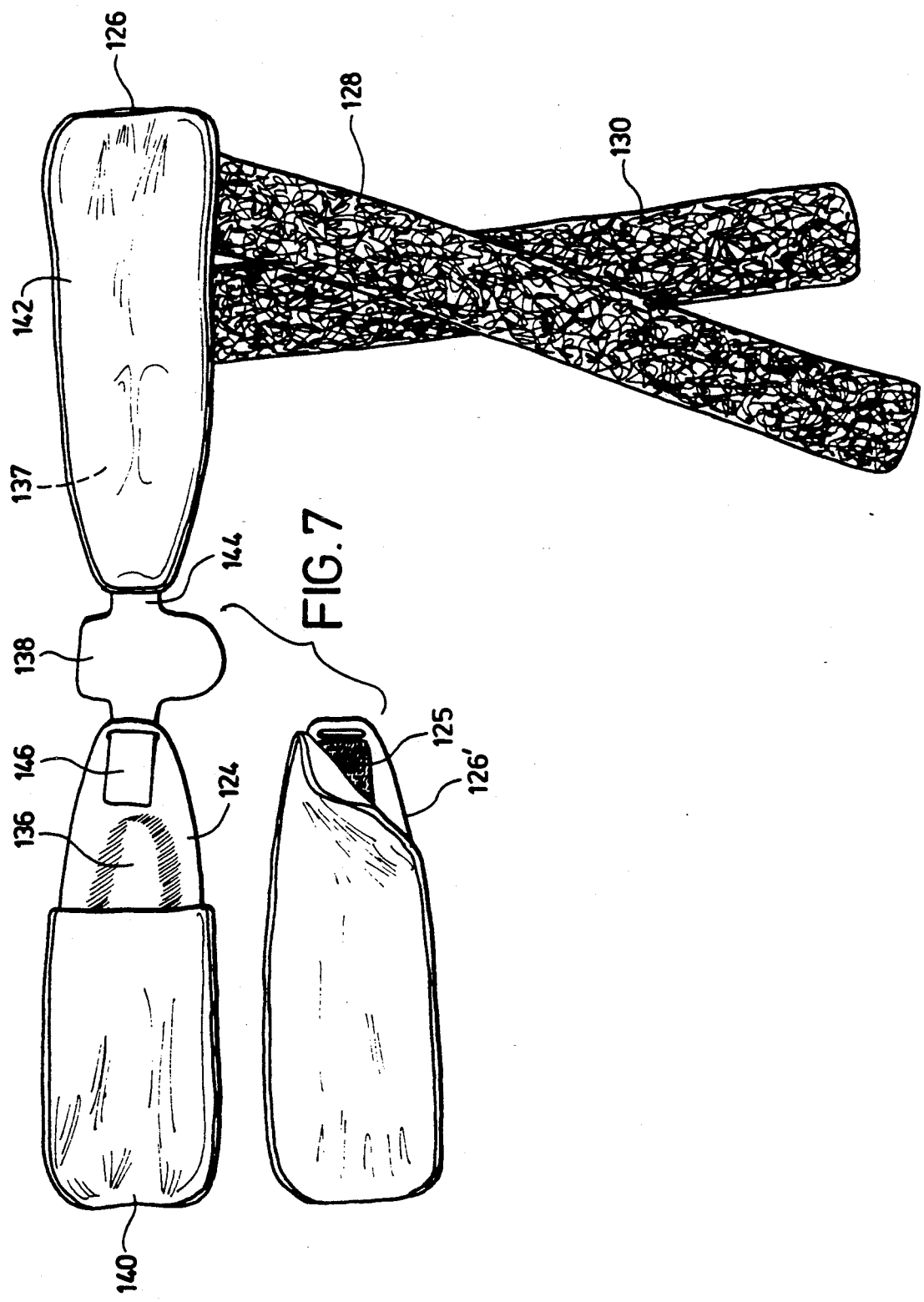

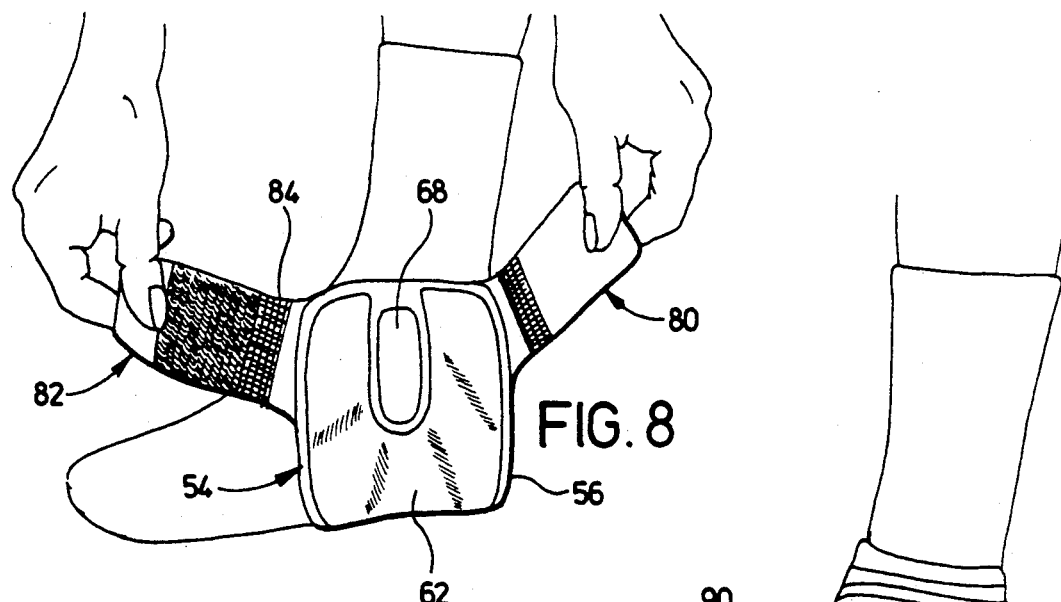
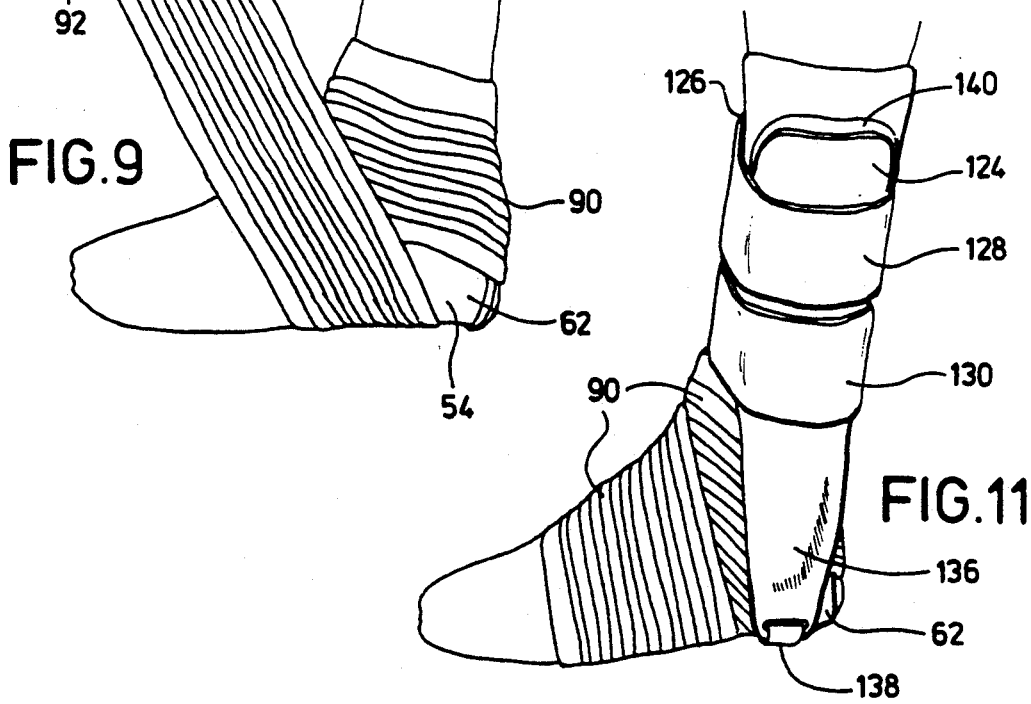

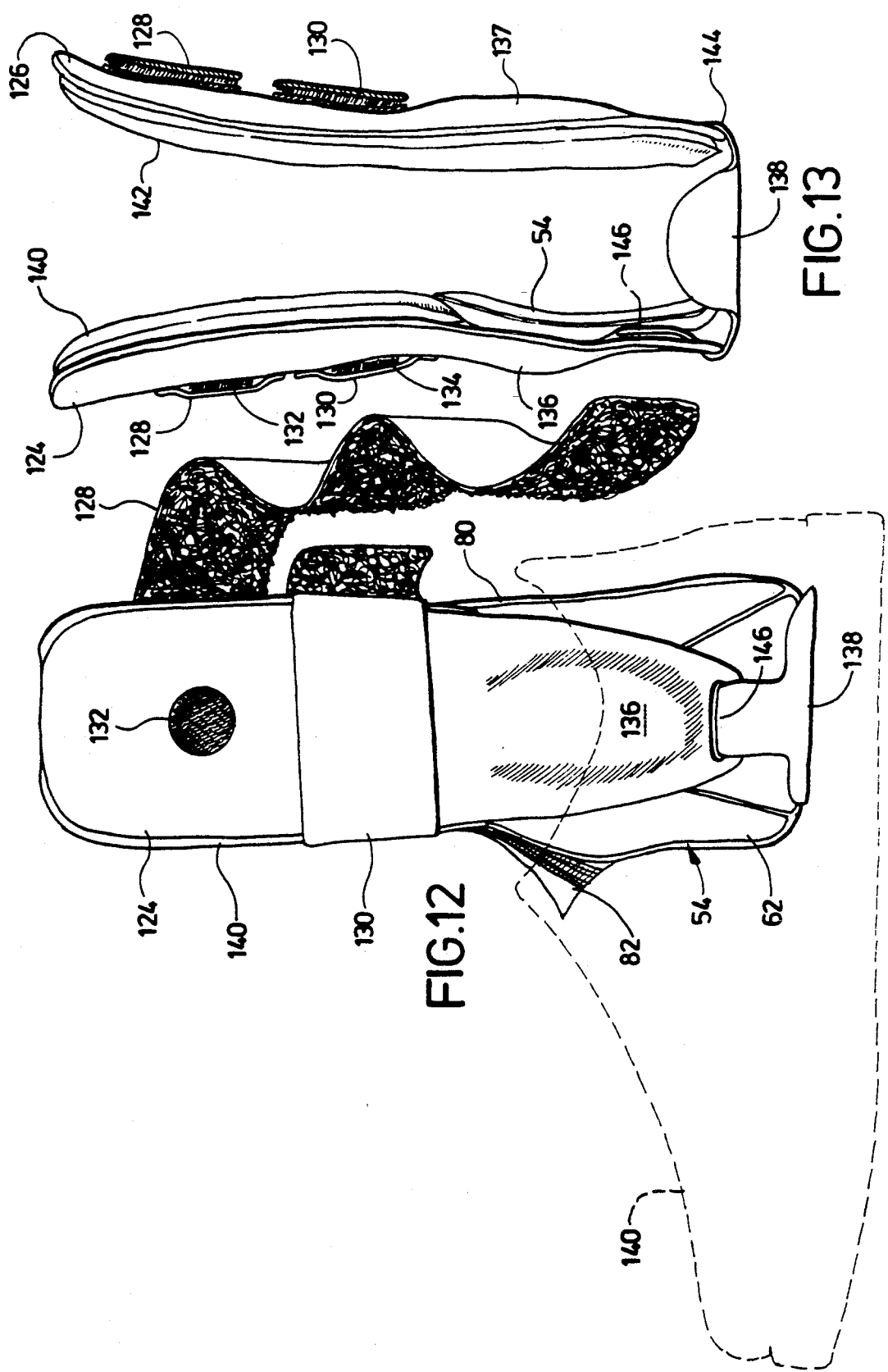

ANKLE SPRAIN MANAGEMENT SYSTEM

FIELD OF THE INVENTION

This invention relates generally to systems used in the application of heat or cold to various injured portions of the human body. In particular, the invention relates to a compress and system for applying hot or cold temperatures to an injured ankle of the human body and relates to a compress designed to be fitted about the ankle to improve the application of the hot or cold temperatures to an injured area.

The human ankle may be injured by strains, contusions, bruises, degenerative joint diseases, arthritis, and arthroscopic operations. Such injuries may cause hematomas and inflamed areas that need to be treated. In such cases, it has been found advantageous to apply a compress of some type to the injured area to effect more rapid healing. In some cases, the compress may include a cold, or sometimes hot, substance. Where a cold substance is required, ice packs have been used and more recently a compress of some type has been used that is filled with a cold liquid and the compress is then applied to the injured area. Some devices such as that disclosed in U.S. Pat. No. 3,900,035 form an elastic bandage for an ankle. The bandage has a shape to receive a foot and has a plurality of liquid pockets embedded in the elastic bandage to fit tightly to the foot and around the ankle. The pockets are filled with a material that can be cooled or heated.

In U.S. Pat. No. 3,548,819, a body splint is formed for use about the wrist to apply thermal pressure thereto. It has two chambers, one filled with a liquid to be placed next to the injured portion of the body and the second to receive air to compress the liquid against the affected part of the body. There are also U-shaped ankle stabilizers which include a U-shaped pad that is open at the top and that has an elongated strap at the bottom for wrapping around the foot and the ankle to hold the U-shaped pad. It is used with a sleeve that fits on the foot and has Velcro strips to which the U-shaped pad is attached. Another cyrotherapy compress bandage utilizes a separate U-shaped cooling element that slips into a harness for strapping around the leg and holding the cooling element close to the ankle. This device has a very complex harness that actually comes between the cooling element and the affected part of the body. All of these devices are in a form generally rectangular bladders or U-shaped bladders which have either a filling cap through which the liquid is inserted or which has the liquid permanently sealed inside a cavity. With all of these devices, it is difficult to secure the bladder properly to the affected area so that proper healing can take place. Further, some of these devices have straps at fixed angles and have to accommodate many different sizes of ankles. Friction points result in some circumstances because the straps must be flexed to adjust an angle. Further, fixed straps do not always allow for complete overlap of the Velcro area and the exposed Velcro may rub against any outer garment and is a source of irritation.

In addition, where there is injury to an ankle, it is important that the compress be so constructed as to provide an open channel to accommodate the medial malleolus of the tibia and preserve the open channel for upward passage of edema. Some of the devices have within them a chamber for containing a liquid and fasteners on the edges of the chamber allow it to be positioned over a particular body portion. Some of the devices allow the liquid to be frozen by placing the device filled with the liquid in a conventional freezer compartment. The frozen package is then attached to the affected part of the body. These devices are disadvantageous because the frozen liquid prevents the bag from conforming to the shape of the affected area. Other devices have a relatively thin bladder which allows the thin layer of ice to be broken into smaller particles so that the bladder can be shaped to the area against which it is placed.

In U.S. Pat. No. 4,280,489, incorporated herein by reference in its entirety, there is provided an ankle brace which has a generally U-shaped stirrup member having a base portion and a pair of opposed side wall portions attached to the base portion. A pair of air-inflatable liners or air bags are disposed interiorly of the stirrup member in juxtaposed relationship to the side wall portions and extend in a substantially coextensive manner therewith. By this arrangement, when the stirrup member is fitted about the lower extremity of the leg, the side wall portions engage the lateral and medial portions of the lower extremity. A plurality of fastener straps are provided to maintain the side wall portions of the stirrup member snugly fitted about the lower leg above the ankle. Means are provided for facilitating inflation of each air bag after the stirrup member has been fitted about the lower extremity and the fastener straps have been engaged. With this device, the foot and the attached stirrup member can be inserted in a shoe so as to provide a brace for the ankle to allow it to heal.

While the above-described devices illustrate a steady improvement in the art for treatment of body injuries, and in particular for a treatment of ankle injuries, they are still lacking in many respects. For instance, there is still a problem with getting a thermal compression device to adequately contact the injured area of the body in a uniform manner. Further, in the treatment of ankle injuries, it is well known that it is medically desirable to enable the edema from the treated area to move upwards. Also, it is desirable to provide forefoot compression to aid in the control of edema.

The present invention relates to an improved ankle sprain management system including a thermal compress that may be used to treat an injured ankle. The improved thermal compress for treatment of an ankle injury includes a U-shaped pad having a compartment of flexible material that is divided into inner and outer compartments, each compartment having an outer wall and a common inner wall. The flexible material may be a vapor barrier material such as that marketed by Uretek, Inc. as part No. 1548-212. It is a 5 mil laminated sandwich having a 2 mil layer of urethane, a 1 mil layer of nylon and a 2 mil layer of urethane. The inner compartment receives a first thermally conductive liquid, such as a salt water and gel compound available from Physicians and Nurses Mfg., Inc. and comprising 95% water and table salt, 4.9% Cellusize (HEC QP5200), blue coloring dye (food grade) and less than .0.05% trace/portion of Ucarcide (250 preservative). This compound will not freeze at generally 32° F. (hereinafter called a "nonfreezing liquid") and is adapted for abutting contact with the ankle. The outer compartment contains a second liquid that freezes generally at 32° F. and is in temperature transfer relationship with the first nonfreezing liquid through the common wall. The open center portion of the U-shaped compress accommodates the fibular malleolus and provides an unrestricted open channel for the upward passage of edema. The inner upper ends of the sides of the U-shaped compress are connected by flexible means to assist in maintaining the U-shape of the compress upon freezing of the second liquid. In one embodiment, the flexible means connect inner upper ends of the sides of the U-shaped compress such that the upper ends of the legs are held closer together than the lower end of the legs to force a three-dimensional shape to the compress for better conformation of the compress about the ankle and to help the U-shape compress keep the shape of the "U" after freezing of the second liquid. The outer compartment of the novel compress is subdivided into multiple smaller compartments each coupled to another by a restricted opening sufficiently small to allow frozen liquid therein to be easily broken to allow the compress to conform generally to the shape of the ankle. Stretchable elastic straps are coupled to the top and bottom of the U-shaped compress for extension around the leg and foot to hold the compress in place against the ankle. The straps have narrowed hook Velcro areas thus allowing for more complete overlap of the loop areas and less problems with Velcro hooks rubbing against outer garments.

While the novel compress can be used by itself, use in combination with a stirrup such as set forth in U.S. Pat. No. 4,280,489 is far preferable. This is because of the protection from reinjury and the additional compression and insulation provided by the stirrup. However, with the normal aircell on the inside of each of the side wall portions of the stirrup, there is simply too much bulk to be worn in the shoe with the novel compress around the ankle. The present invention modifies the aircell on one of the side wall portions of the stirrup so that aircell covers only the proximal half of the side wall, thus leaving the distal half open to receive the bulk of the compress. A flexible base portion couples the distal ends of the side wall portions to form the generally U-shaped stirrup member for receiving the heel of the foot. That side wall portion that contains the aircell covering only its proximal half is detachably coupled at its distal end to the flexible base portion. Therefore, in the acute phase of the injury, the present invention including the modified side wall is worn over the compress. When the swelling and edema are resolved and the compress is no longer needed, the modified side wall of the stirrup is replaced with the standard side wall having an aircell that covers the entire inner side of the side wall portion and the stirrup is worn normally during the rehabilitation phase.

Thus, it is an object of the present invention to provide a novel compress that includes a U-shaped thermal compress that, in the preferred embodiment, has a short elastic strap attached to either the anterior or posterior edge of the upper outer sides of the U. The strap is wrapped around the ankle and attached to a narrow Velcro strip on the other edge to hold the U-shaped pad in place and also serves to tension the legs of the U away from each other so as to preserve the open channel between the legs. The unrestricted open channel is important for the upward passage of edema.

It is also an object of the present invention to provide, in the preferred embodiment, an elongated elastic strap that is attached to the bottom edge of the U-shaped pad. Its purpose is to further compress the U-shaped pad and to add compression to the forefoot for the control of edema. It is wrapped first under the foot to the medial side then over the front of the ankle, over the U-shaped pad to the back of the ankle and then around the medial side and spiral wrapped several turns around the foot toward the forefoot.

It is still another object of the present invention to provide a gel compound as the nonfreezing liquid in the inner chamber that abuts the ankle. Gel has a lower vapor transmission rate through the plastic and its viscosity is such as to provide a conforming contact with the ankle.

It is also an object of the present invention to construct the U-shaped pad into a semi-three-dimensional shape for better conformation around the ankle.

It is a further object of the present invention to provide an enhanced, graduated ankle sprain management. During the acute phase of the injury, the stirrup can be used with the compress and the entire management system attached to the foot and lower portion of the leg and inserted in a shoe. When the swelling and edema are resolved and the compress is no longer needed, the modified side wall of the stirrup is replaced with a standard side wall so that the stirrup is worn normally during the rehabilitation phase without the compress.

SUMMARY OF THE INVENTION

Thus, the present invention relates to a thermal compress for the ankle comprising a U-shaped fluid impervious compartment of flexible material that is divided into inner and outer chambers, each chamber having an outer wall and a common inner wall, the inner chamber receiving a first thermally conductive nonfreezing liquid and adapted for abutting contact with the ankle; the outer chamber containing a second liquid that maintains a cold temperature, as by freezing, in temperature transfer relationship with the first nonfreezing liquid through the common wall. The U-shaped center portion accommodates the fibular malleolus and provides an unrestricted open channel for the upward passage of edema. A flexible connection between the inner upper ends of the sides of the U-shaped compartment assists in maintaining the U shape of the compress upon freezing of the second liquid. The outer chamber is subdivided into multiple smaller chambers each coupled to another by a restricted opening sufficiently small to allow frozen second fluid therein to be easily broken to allow the multiple smaller chambers to move with respect to each other and allow the compress to be conformed generally to the shape of the ankle. Stretchable elastic straps are coupled to the top and the bottom of the U-shaped compartment for extension around the leg and foot to hold the compress in place against the ankle.

In the preferred embodiment, a strip of stretchable fabric extends upwardly at an angle from at least one outer side of the upper end of the U-shaped compress to pass around the leg and attach to the other side of the compress to hold the upper end of the compress against the ankle while simultaneously providing tension to the upper ends of the legs of the U to preserve the open channel between the legs of the U. The strap and compress have matching Velcro strips thereon to attach the strap to the compress together after being wrapped around the leg above the ankle. Also in the preferred embodiment, an elongated stretchable strap is attached to the lower end of the U-shaped compartment and has sufficient length to wrap under the foot and around the ankle over the U-shaped compress to securely hold the compress in place about the ankle and add compression to the forefoot for the control of edema.

Additionally, a pair of spaced-apart side wall portions are adapted to mate with corresponding side portions of the lower leg and ankle. A flexible base portion couples the distal ends of the side wall portions to form a generally U-shaped stirrup member for receiving the heel of the foot. A first flexible support member is substantially coextensively disposed in a juxtaposed relationship with only the proximal half of the inwardly facing surface of the first side wall portion such that the inwardly facing surface of the distal half of the side wall portion is disposed over the compress to provide protection of the ankle from reinjury and to provide additional compression and insulation. A second flexible support member is substantially coextensively disposed in a juxtaposed relationship with respect to the inwardly facing surface of the second side wall portion so as to engage a corresponding mating side portion of the leg and ankle. Fastening means are coupled to the side wall portions for maintaining the first and second flexible support members in engagement with the compress and corresponding mating side portions of the lower leg and ankle when the U-shaped stirrup member receives the heel of the foot.

BRIEF DESCRIPTION OF THE DRAWINGS

These and other objects of the present invention will be more fully understood in conjunction with the detailed description and the accompanying drawings in which like numerals represent like elements and in which:

FIG. 1 is a diagrammatic representation of the front view of the preferred embodiment of a thermal compress utilizing a U-shaped thermal compress;

FIG. 2 is a back view of the preferred embodiment of the compress illustrated in FIG. 1;

FIG. 3 is a cross-sectional view of the preferred embodiment of the thermal compress illustrated in FIG. 1;

FIG. 4 is a back view of the novel U-shaped compress before it has been filled with fluid and the straps attached;

FIG. 5 is a back view of the novel U-shaped compress illustrating the upper ends of the U being attached to each other such that the upper ends of the legs of the U are closer together than the bottom ends of the legs;

FIG. 6 is a cross-sectional view of the U-shaped pad in FIG. 5 taken along lines 6—6 to illustrate the three dimensional effect given to the compress by fastening the upper ends of the legs of the U closer together than the bottom ends of the legs;

FIG. 7 is an unfolded plan view in reduced scale of the stirrup member of the present invention illustrating the modified side wall and the standard side wall;

FIG. 8 is a side view of the compress being attached to the injured ankle;

FIGS. 9 and 10 illustrate the completion of the attachment of the compress to the ankle;

FIG. 11 is a side view of the ankle sprain management system attached to the ankle and leg including the U-shaped stirrup member having a modified side wall portion over the compress;

FIG. 12 is a side view of the entire management system when the foot is placed in a shoe; and FIG. 13 is an end view of the novel management system shown in FIG. 11.

DETAILED DESCRIPTION OF THE DRAWINGS

While the novel thermal compress of the present invention can be used to apply cold or hot temperatures to the human body, it will be described herein with respect to providing a cold temperature where its greatest use is anticipated. The preferred embodiment is illustrated in FIGS. 1-5. It can be seen in FIG. 1 that the thermal compress 54 comprises a U-shaped fluid impervious compartment 56 of flexible material with outer walls formed of a fluid impervious flexible material such as a thermoplastic material. Suitable thermoplastics are plasticized polyethylene, plasticized polyvinyl chloride, plasticized polyvinyl acetate and the like. Another material may be the 5 mil laminated vapor barrier material mentioned earlier that is sold by Uretek, Inc. as Part No. 1548-212. The compartment 56 is divided into inner and outer chambers 58 and 60, respectively, as illustrated in FIG. 3. Each chamber 58 and 60 has an outer wall 62 and 64, respectively, and a common inner wall 66 which, preferably, is also a thermoplastic material. The inner chamber 58 receives approximately 70 cc's of a thermally conductive liquid such as a salt water gel compound described previously that does not freeze at the same temperature as the fluid in outer chamber 60 and is adapted for abutting contact with the ankle. The gel may be of the type such as used in shampoos and designated DuPont Hydro Gel. It has a low vapor transmission rate through the plastic walls. The outer chamber 60 contains approximately 60 cc's of a second liquid (such as water that can be frozen) in temperature transfer relationship with the first nonfrozen liquid gel through the common wall 66. The elongated open center portion 68 accommodates the fibular malleolus and provides an unrestricted open channel for the upward passage of the edema. A flexible plastic area 70 formed from the plastic welding of the two outer walls 62 and 64 with common wall 66 connects the inner upper ends 72 and 74 of the sides of the U-shaped compartment 56 to assist in maintaining the U shape of the compress upon freezing of the second liquid such as water. The outer chamber 60 is subdivided into multiple smaller chambers 76 each coupled to another by a restricted opening 78 sufficiently small to allow the second fluid, when frozen, to be easily broken in the restricted opening areas 78 to allow the compress 56 to conform generally to the shape of the ankle. This occurs because there are essentially five smaller compartments or chambers 76 in the outer chamber 60 that can each be flexed with respect to the other in the restricted area 78 when the frozen liquid therein is broken so that the compress can conform itself generally to the shape of the ankle.

Strap 80 is of stretchable fabric such as Velcro compatible spandex (elastic) and extends upwardly at an angle from outer side 84 of the upper end of the U-shaped compartment 56 to tension the upper ends of the legs of the U away from each other and preserve the open channel between the legs of the U when strap 80 is wrapped about the ankle. Strap 82 is a relatively narrow 1¾ hook mating Velcro strip attached to the other side to connect the straps 80 and 82 together after being wrapped around the leg above the ankle. The narrow Velcro strip allows for a more complete overlap of strap 80 over the Velcro strip 82 thus obviating the problem of Velcro hooks rubbing against outer garments. An elongated stretchable strap 90 is attached to the lower end of the U-shaped compartment 56 preferably by being permanently attached thereto and has sufficient length to wrap under the foot and around the ankle over the U-shaped compress several times to securely hold the compress in place about the ankle and add compression to the forefoot for the control of edema. The elongated strap 90 is made entirely of a first Velcro compatible material with a strip of second matching hook Velcro material 92 on the end thereof such that when it is wrapped several times around the ankle, it will adhere to itself. As shown in the reverse view in FIG. 2 a layer of soft insulating material 96 such as brushed tricot (nylon) fabric is attached to the outside wall 64 of the outer U-shaped chamber 60 in superimposed relationship to provide a thermal barrier that inhibits rapid temperature change of the frozen fluid in chamber 60 due to ambient temperature. Again, the first thermally conductive liquid that is not frozen is preferably a gel. The flexible plastic area 70 that connects the inner upper ends 72 and 74 of the legs of the U-shaped compress 56 holds the upper ends of the legs closer together than the lower end of the U-shaped portion of the legs as illustrated by the arrows 98 and 100 to force a three-dimensional shape of the compress as shown in FIG. 6 for better conformation of the compress 56 about the ankle and to help the U-shaped compress 56 keep the shape of the U after it is frozen. Again, the U-shaped compress 56 has an elongated open center portion 68 formed between the legs of the U-shaped compartment for accommodating the fibular malleolus and providing an unrestricted open channel for the upward passage of edema.

The U-shaped compress 56 is shown as a blank in FIGS. 4 and 5 prior to filing the chambers 58 and 60 with fluid and prior to adding straps 80, 82 and 90. The tabs 102 and 104 in FIG. 4 are brought into overlapping relationship with each other and then plastic welded. The overlapping relationship creates the narrower upper end of the elongated open center portion 68 as illustrated by arrow 98 in FIG. 5. As stated earlier, that construction causes the lower end of the compress 56 to bow outwardly and assume a three dimensional shape as shown in FIG. 6 that allows the compress 56 to better conform to the shape of the ankle.

The extension 106 shown at the bottom of the compress 56 includes all four layers 62, 64, 66 and 96 and is plastic welded on the sides only. This allows a needle to be inserted through extension 106 into chambers 58 and 60 to inject respectively the gel compound and liquid such as water therein. The extension 106 is then plastic welded. The elongated strap 90 is then heat welded to tabs 108 and 110 and extension 106. Straps 80 and 82 are heat welded to upper extension 84 to form the completed compress assembly of the preferred embodiment.

While the novel compress could be used by itself, its use in combination with the stirrup such as that disclosed in U.S. Pat. No. 4,280,489 is far preferable. This is because the U-shaped stirrup provides protection of the ankle from reinjury and provides additional compression and insulation.

FIG. 7 is a plan view of the novel U-shaped stirrup that is formed of a pair of side wall portions 124 and 126 adapted to mate with corresponding side portions of the lower leg and ankle. A flexible base portion 138 couples the distal ends of the side wall portions 124 and 126 to form a generally U-shaped stirrup member for receiving the heel of the foot as shown in FIG. 13. A first flexible support member 140 is substantially coextensively disposed in juxtaposed relationship with only the proximal half of the inwardly facing side of the side wall portion 124 such that the inwardly facing surface of the distal half of the side wall portion may be disposed over the compress shown in FIGS. 1 and 13 to provide protection of the ankle from reinjury and provide additional compression and insulation. A second flexible support member 142 is substantially coextensively disposed in a juxtaposed relationship with respect to the inwardly facing surface of the second wall portion 126 so as to engage a corresponding mating side portion of the leg and the ankle. End 144 of flexible base portion 138 may be fixedly attached to side wall portion 126 while end 146 may be removably attached to the distal end of the side wall portion 124 as by hook and loop systems such as Velcro strip 125. This enables the side wall 124 to be removed and replaced with an alternate side wall portion 126' similar to that represented by side wall portion 126 so that the compress can be removed and the entire mating side portion of the leg and ankle on both sides can be covered. FIGS. 8, 9, 10 and 11 illustrate the compress 54 being attached to the ankle with straps 80 and 82 and the malleolus exposed in the opening 68. The strap 90 is wrapped around the foot and ankle as shown to apply focused compression to the areas of traditional swelling surrounding the lateral malleolus. As stated previously, the open U in the compress 54 provides a low pressure passageway for dissipation of edema to the leg above and the wrap 90 controls forefoot migration.

In FIG. 11, the pair of spaced-apart side walls 124 and 126 are illustrated on the outside of and covering the compress 54. Because only the proximal half of the inwardly facing surface of the side wall portion 124 has the flexible support member thereon, the distal half of the side wall portion 124 is disposed over the compress 54 to provide protection of the ankle from reinjury and to provide additional compression and insulation. The entire foot, compress and side wall portions can be inserted in a shoe 140 as illustrated in FIG. 12. Concave portion 136 of side wall 124 accommodates the malleolus.

FIG. 13 is an end view of the spaced-apart side wall portions 124 and 126 joined by the flexible base portion 138 at the distal ends thereof to form a generally U-shaped stirrup member for receiving the heel of the foot. As can be seen in FIG. 13, a first flexible support member 140 is substantially coextensively disposed in a juxtaposed relationship with only the proximal half of the inwardly facing surface of side wall portion 124 such that the inwardly facing surface of the distal half of the side wall portion 24, including concave area 136, is disposed over compress 54 to provide protection of the ankle. Because the distal half of side wall portion has no flexible support member, it can accommodate the compress 54 and still allow the entire assembly to be inserted with the foot in a shoe as illustrated in FIG. 12. Side wall portion 126 can be seen to have a second flexible support member 142 substantially coextensively disposed in a juxtaposed relationship with respect to its inwardly facing surface so as to engage a corresponding mating side portion of the leg and ankle.

Thus, the present system allows a unique method of managing an ankle sprain that includes swelling and edema. First, the thermal compress 54 is attached in a conformed relationship to the injured side of the ankle during the swelling and edema stage of the sprain. The second step comprises mating first and second spaced-apart side wall portions in conforming relationship with corresponding side portions of the lower leg and ankle, the first side wall portion having a substantially coextensively disposed first flexible support member in a juxtaposed relationship with only the proximal half of the inwardly facing surface of the first side wall portion such that the first flexible support member engages a corresponding portion of the leg above the ankle and such that the inwardly facing surface of the distal half of the first side wall portion is disposed over the thermal compress to provide protection of the ankle from reinjury and to provide additional compression and insulation, said second side wall portion having a substantially coextensively disposed second flexible support member in juxtaposed relationship with respect to the inwardly facing surface of the second wall portion so as to engage a corresponding mating side portion of the leg and ankle, and the third step comprises maintaining the first and second flexible support members in engagement with the compress and the corresponding mating side portions of the lower leg and ankle.

The method further includes the steps of coupling the distal ends of each side wall portion with a flexible base portion to form a generally U-shaped stirrup member for receiving the heel and foot, removably attaching one end of the flexible base portion to the distal end of the first side wall portion and fixedly attaching the other end of the flexible base portion to the distal end of the second side wall portion.

The method also includes the steps of detaching the removably attached first side wall portion from the flexible base portion when the swelling and edema are resolved, removing the thermal compress from the ankle, removably attaching a third side wall portion at its distal end to the flexible base portion, said third side wall portion having a third flexible support member coextensively disposed in juxtaposed relationship with respect to the inwardly facing surface of the third wall portion so as to engage a corresponding mating side portion of the leg and ankle, and maintaining the second and third flexible support members in engagement with the corresponding mating side portion of the lower leg and ankle.

Thus, there has been disclosed a novel thermal compress, which, in the preferred embodiment, is a unitary structure having a substantially U-shaped compartment subdivided into two chambers separated by a common wall. One of the chambers has therein a liquid to be frozen such as water and the other has a liquid that is not to be frozen such as a gel. The gel side or chamber of the compress is placed against the ankle and there is an oval shaped center portion therein to accommodate the medial malleolus. The chamber containing the frozen liquid is subdivided into multiple smaller chambers separated from each other by restricted openings that, when they contain ice, allow the ice to be easily broken. The multiple smaller chambers can then better conform to the ankle shape. An elongated passageway includes the oval shaped open center portion and extends upwardly between the legs of the U-shaped compress to provide an open channel for unrestricted passage of edema in the upward direction. At the upper end of the legs of the U-shaped compress, a strip of stretchable fabric extends upwardly at an angle from the top of one outer side to tension the upper ends of the legs of the U away from each other and to preserve the open channel between the legs of the U as it passes around the leg above the ankle and is attached to the other side. The novel elongated stretchable strap attached to the lower end of the U-shaped compartment has sufficient length to wrap around the foot and under the ankle over the U-shaped compress several times to securely hold the compress in place about the ankle and add compression to the forefoot for the control of edema.

There has also been disclosed a novel ankle sprain management system having a pair of spaced-apart side wall portions adapted to mate with corresponding side portions of the lower leg and ankle. A flexible base portion couples the distal ends of the side wall portions to form a generally U-shaped stirrup member for receiving the heel of the foot. A first flexible support member is substantially coextensively disposed in a juxtaposed relationship with only the proximal half of the inwardly facing surface of a first side wall portion such that the inwardly facing surface of the distal half of the side wall portion is disposed over the compress placed around the ankle to provide protection of the ankle from reinjury and provide additional compression and insulation. A second flexible support member is substantially coextensively disposed in a juxtaposed relationship with respect to the inwardly facing surface of the second side wall portion so as to engage a corresponding mating side portion of the leg and ankle. Fastening means are coupled to the side wall portions for maintaining the first and second flexible support members in engagement with the compress and corresponding mating side portions of the lower leg and ankle when the U-shaped stirrup member receives the heel of the foot. The first one of the side wall portions is removably attached to the flexible base portion so that when the swelling and edema are controlled the compress can be removed and a third side wall portion substantially identical to the second side wall portion can be attached to the flexible base portion to form a U-shaped stirrup with flexible support members to protect the ankle.

The foregoing specification describes only the embodiment of the invention shown and/or described. Other embodiments may be articulated as well. The terms and expressions used, therefore, serve only to describe the invention by example and not to limit the invention. It is expected that others will perceive differences which, while different from the foregoing, do not depart from the scope of the invention herein described and claimed. In particular, any of the specific constructional elements described may be replaced by any other known element having equivalent function.

What is claimed is.

1. An ankle sprain management system comprising:
   a U-shaped fluid impervious compartment of flexible material forming a compress, the compress being divided into inner and outer chambers, each chamber having an outer wall and a common inner wall;
   said inner chamber receiving a first thermally conductive fluid and adapted for abutting contact with the ankle;
   said outer chamber containing a second fluid that freezes before said first liquid and that is in temperature transfer relationship with the first fluid through the common wall;
   said outer chamber being subdivided into multiple smaller chambers each coupled to another by a restricted opening sufficiently small to allow the second fluid frozen therein to be easily broken to enable said compress to conform generally to the shape of the ankle;
   an open center portion formed between the legs of the U for accommodating the fibular malleolus and providing an unrestricted open channel for the upward passage of edema;

flexible means joining the inner upper ends of the sides of the U-shaped compartment to assist in maintaining the U shape of the compress upon freezing of the second fluid; and stretchable elastic straps coupled to the top and the bottom of the U-shaped compartment for extension around the leg and foot to hold the compress in place against the ankle.

2. A compress as in claim 1 wherein the first thermally conductive fluid is a gel compound.

3. A compress as in claim 1 wherein the stretchable elastic straps comprise:

a length of stretchable fabric extending upwardly at an angle from one outer side of the upper end of the U-shaped compartment to connect to the other side and tension the upper ends of the legs of the U away from each other to preserve the open channel between the legs of the U, said strip having Velcro thereon to attach to the other side of the compartment after being wrapped around the leg above the ankle; and an elongated stretchable strap attached to the lower end of the U-shaped compartment and having sufficient length to wrap under the foot, across the forefront, around the ankle and over the U-shaped compress to securely hold the compress in place about the ankle and add compression to the forefoot for control of edema.

4. A compress as in claim 3 wherein the elongated strap is made entirely of a first Velcro-like loop material with a second matching Velcro hook material on the end thereof so that the end of the elongated strap can be attached to the remainder of the strap at any point.

5. A compress as in claim 4 further comprising a layer of soft insulating material attached to the outside of the outer U-shaped compartment in superimposed relationship to provide a thermal barrier that inhibits rapid temperature change of said second frozen fluid due to ambient temperature.

6. A compress as in claim 5 wherein the first thermally conductive fluid is a gel compound.

7. A compress as in claim 6 wherein said flexible means connecting the inner upper ends of the legs of the U-shaped compress hold the upper ends of the U-shaped portion of the legs closer together than the lower end of the legs to create a three-dimensional shape for better conformation of the compress about the ankle and to help the U-shaped compress keep the shape of the U after the second fluid is frozen.

8. An ankle sprain management system as in claim 1 further comprising:

a pair of spaced-apart side wall portions adapted to mate with corresponding side portions of the lower leg and ankle;

a flexible base portion coupling the distal ends of the side wall portions to form a generally U-shaped stirrup member for receiving the heel of the foot;

a first flexible support member being substantially coextensively disposed in a juxtaposed relationship with only the proximal half of the inwardly facing surface of a first one of the side wall portions such that the inwardly facing surface of the distal half of the first side wall portion is disposed over said compress to provide protection of the ankle from reinjury and to provide additional compression and insulation;

a second flexible support member being substantially coextensively disposed in a juxtaposed relationship with respect to the inwardly facing surface of the second one of the side wall portions so as to engage a corresponding mating side portion of the leg and ankle; and fastening means coupled to the side wall portions for maintaining the first and second flexible support members in engagement with the compress and corresponding mating side portions of the lower leg and ankle when the U-shaped stirrup member receives the heel of the foot.

9. A system as in claim 8 in which the first one of the side wall portions is removably attached to the flexible base portion.

10. A system as in claim 9 wherein each of the first and second side wall portions is formed of injection molded thermoplastic material.

11. A system as in claim 10 wherein each side wall portion has a recess for receiving a corresponding malleolus on the ankle.

12. A system as in claim 11 wherein each of the first and second support members is an inflatable bladder adapted to be inflated to a predetermined pressure to form a pressurized cushion between the side wall portions and the corresponding portions of the lower leg and ankle.

13. A system as in claim 12 wherein the flexible base portion is a strip of woven material.

14. A system as in claim 13 wherein the flexible strip is removably attached to the first one of the side wall portions with hooks and loops.

15. A system as in claim 14 wherein the hooks are integrally formed with the first side wall portion during the injection molding thereof.

16. A thermal compress for applying cold and compression to swollen and inflamed areas of the ankle, including areas of edema comprising:

a U-shaped fluid impervious compartment of flexible material;

a fluid impervious common wall separating the compartment into inner and outer chambers, the inner chamber receiving a first thermally conductive fluid and adapted for abutting contact with the area of the ankle to be treated;

the outer chamber containing a second fluid that freezes before the first fluid, the second fluid being in temperature transfer relationship with the first liquid through the common wall;

an elongated oval open center portion between the legs of the U-shaped compartment accommodating the fibular melleolus and providing an unrestricted open channel for the upward passage of edema;

flexible means connecting the inner upper ends of the legs of the U-shaped compartment closer together than the lower ends of the legs to create a three-dimensional shape of the U-shaped compartment that provides conformation of the compress about the ankle area and helps the compress keep the shape of a U after the second fluid is frozen; and the outer chamber being subdivided into multiple smaller chambers each coupled to another by a restricted opening for receiving the second fluid, the restricted openings being sufficiently small to allow frozen fluid therein to be easily broken to enable the compress to conform generally to the shape of the ankle.

17. A compress as in claim 16 further comprising a layer of soft insulating material attached to the outside of the outer chamber in superimposed relationship to provide a thermal barrier from ambient air for the second chamber.

18. A method of managing an ankle sprain comprising the steps of:
- attaching a thermal compress in a conformed relationship to an injured side of the ankle during the swelling and edma stage of the sprain;
- mating inwardly facing surfaces of first and second spaced-apart side wall supports in conforming relationship only with corresponding side portions of the lower leg and ankle, said first side wall support having a substantially coextensively disposed first flexible support member in a juxtaposed relationship with only the proximal half of the inwardly facing surface of the first side wall support such that the first flexible support member engages a corresponding portion of the leg above the ankle and such that the inwardly facing surface of the distal half of the first side wall support is disposed over the thermal compress to provide protection of the ankle from reinjury and to provide additional compression and insulation;
- said second side wall support having a substantially coextensively disposed second flexible support member in juxtaposed relationship with respect to the inwardly facing surface of the second wall support so as to engage a corresponding mating side portion of the leg and ankle; and
- maintaining the first and second side wall supports in supporting engagement with the compress and the corresponding mating side portions of the lower leg and ankle.

19. A method as in claim 18 further including the steps of:
- coupling the distal ends of each side wall support with a flexible base portion to form a generally U-shaped stirrup member for receiving the heel and foot;
- removably attaching one end of the flexible base portion to the distal end of the first side wall support; and
- fixedly attaching the other end of the flexible base portion to the distal end of the second side wall support.

20. A method as in claim 19 further comprising the steps of:
- detaching the removably attached first side wall support from the flexible base portion when the swelling and edema are resolved;
- removing the thermal compress from the ankle;
- removably attaching a third side wall support at its distal end to the flexible base portion, said third side wall support having a third flexible support member coextensively disposed in juxtaposed relationship with respect to the inwardly facing surface of the third side wall support so as to engage a corresponding mating side portion of the leg and ankle; and
- maintaining the second and third flexible support members in engagement with the corresponding mating side portions of the lower leg and ankle.

* * * * *